United States Patent [19]

Ryf

[11] 3,950,445

[45] Apr. 13, 1976

[54] PROCESS FOR THE PRODUCTION OF BENZOTRIFLUORIDE

[75] Inventor: Kurt Ryf, Visp, Wallis, Switzerland

[73] Assignee: Lonza Ltd., Gampel, Valais, Switzerland

[22] Filed: Dec. 23, 1974

[21] Appl. No.: 536,973

[30] Foreign Application Priority Data

Dec. 21, 1973 Switzerland............... 17987/73

[52] U.S. Cl............................................. 260/651 F
[51] Int. Cl.$^2$....................................... C07C 25/14
[58] Field of Search.................................. 260/651 F

[56] References Cited
UNITED STATES PATENTS

| | | | |
|---|---|---|---|
| 2,562,159 | 7/1951 | Wojcik et al. | 260/651 F |
| 3,742,074 | 6/1973 | Hermann et al. | 260/651 F |
| 3,859,372 | 1/1975 | Robota | 260/651 F |

*Primary Examiner*—D. Horwitz
*Attorney, Agent, or Firm*—Christen & Sabol

[57] ABSTRACT

The process of preparing benzotrifluoride which involves reacting benzotrichloride with hydrogen fluoride in a reaction zone at a pressure between 20 and 45 atm. and at a temperature between 85° and 100°C. The reaction is conducted in the presence of a catalyst consisting of a mixture of aluminum chloride and activated charcoal. On a stoichiometric basis, the amount of hydrogen fluoride is 1.0 to 1.1 times the amount of the benzotrichloride. The benzotrichloride, catalyst and hydrogen fluoride are present as an admixture or intermixture having a Reynolds number between 65,000 and 100,000. The reaction can be conducted in a stirring vessel equipped with a stirring mechanism.

19 Claims, No Drawings

PROCESS FOR THE PRODUCTION OF BENZOTRIFLUORIDE

BACKGROUND OF THIS INVENTION

1. Field of This Invention

This invention relates to a process for the production of benzotrifluoride.

2. Prior Art

Whitmore, Frank C., "Organic Chemistry," 2nd Ed., D. Van Nostrand Co., Inc., (1951), at page 622, teaches that benzotrichloride, with suitable reagents such as AgF or HF, gives benzotrifluoride. At page 275, Whitmore, ibid., teaches that benzotrifluoride results when benzotrichloride is treated with Ag or Sb fluoride.

Compounds which carry one or more trichloromethyl groups on an aromatic nucleus can be converted using hydrogen fluoride into the corresponding trifluorometyl compounds — see Houben-Weyl, "Methods of Organic Chemistry," vol. 5/3, pp. 121 to 123. However, the industrial practice of such reaction results in large amount of formation, with the result that only irregular and small yields are achieved.

German published Application No. 1,618,390 describes a continuous process which occurs in a flow pipe that involves the use of an excess of hydrogen fluoride of at least one third of the theoretical (stoichiometric) quantity. However, the use of a reaction pipe for the subject reaction has several disadvantages since the developing hydrochlorid acid gas forms a gas cushion in the reaction space thereby considerably reducing the effective reaction volume. Furthermore, in order to achieve the necessary intensive intermixing, a flow of great turbulence must be striven for in the reactor. This has the disadvantage that the narrow cross sections of the pipe, which are necessary for the purpose of this measure, are inclined to plug up as a result of the formation of resin.

German published Application No. 1,965,782 proposes, in order to avoid the undesirable formation of resin, adding hexamethylenetetramine to the reaction mixture. Preferably 5 mole of hydrogen fluoride are used per mole of starting compound and trichloromethyl group. The reaction time according to the example is about 48 hours.

In order to prevent corrosion, a proposal has been made in German published Application No. 2,161,995 to carry out the reaction at a pressure of about 3 to 20 atm. and at a temperature of about 20° to 60°C. For the successful execution of the reaction however, one must use an excess of hydrogen fluoride in a quantity of at least 3 times the quantity required theoretically (stoichiometrically).

The mentioned processes have the disadvantages of needing a large excess of hydrogen fluoride. Both for economic reasons and for reasons of environmental protection, these excesses must be recaptured as much as possible in order to be able to feed them again to the reaction. When slightly smaller excesses of hydrogen fluoride are used one finds that the reaction times are in the range of several days, which of course is likewise detrimental to the economics of the process.

BROAD DESCRIPTION OF THIS INVENTION

An object of this invention is to provide a process for the production of benzotrifluoride which requires little or no excess hydrogen fluoride reactant. Another object of this invention is to provide a process for the production of benzotrifluoride which has a short reaction time. A further object of this invention is to provide a process which has a significatly increased yield and insignificant or minimal resin by-product formation. A still further object of this invention is to provide a process which minimizes the corrosion of the reaction equipment. A further object of this invention is to provide a process which achieves reduced environmental problems.

Other objects and advantages of this invention are set out herein or are obvious herefrom to one ordinarily skilled in the art.

The objects and advantages of this invention are achieved by this invention.

This invention involves a process of preparing benzotrifluoride. The process includes reacting benzotrichloride with hydrogen fluoride in a reaction zone at a pressure between 20 and 45 and at a temperature between 85° and 100°C. in the presence of a catalyst. The catalyst consists of a mixture of aluminum chloride and activated charcoal. On a stoichiometric basis the amount of the hydrogen fluoride being 1.0 to 1.1 times the amount of the benzotrichloride. The benzotrichloride, the catalyst and the hydrogen fluoride are present as an admixture or intermixture. The admixture or intermixture is intensively admixed or intermixed to an extent during the reaction that the admixture or intermixture has a Reynolds number between 65,000 and 100,000. The Reynolds number characterizes the turbelent streaming of the mixture — the kinematic viscosity is set, in essence, by the reaction and cannot be changed.

Preferably the reaction is conducted in a stirring vessel equipped with a stirring mechanism. Preferably the benzotrichloride is placed in the reaction zone, and then the catalyst and the hydrogen fluoride are placed in the reaction zone. Preferably the benzotrichloride is treated with about one percent of phosphorous trichloride, based on the amount of benzotrichloride (before the catalyst and the hydrogen fluoride are added to the reaction zone). The benzotrichloride is preferably heated to the reaction temperature before the catalyst and the hydrogen fluoride are added to the reaction zone. Although excellent results are obtained when the reaction zone is heated to the reaction temperature after the catalyst and the hydrogen fluoride are added to the reaction zone. The pressure in the reaction zone is usually raised to the reaction pressure after the reaction zone is heated to the reaction temperature. Preferably the pressure is raised in the reaction zone to the reaction pressure after addition of the benzotrichloride, the catalyst and the hydrogen fluoride by the introduction of an inert gas. Most preferably the inert gas is nitrogen. Also, the reaction temperature is preferably between 90° and 95°C., and reaction pressure is preferably between 35 and 40 atmospheres. The reaction admixture preferably has a Reynolds number between 80,000 and 90,000 during the reaction.

It is very important that the benzotrichloride, catalyst and hydrogen fluoride be intensively intermixed.

The reaction can be carried out continuously. In such a case the reaction zone can contain two reaction regions, the first reaction region being a first reaction vessel and the second reaction region being a second reaction vessel. The reaction is carried out to a desired stage in the first reaction vessel and then completed in the second reaction vessel after the reaction admixture is transferred from the first reaction vessel to the second reaction vessel. The reaction can also be carried out on a continuous basis where the reaction zone is divided into two reaction regions, the first reaction region being a reaction vessel and the second reaction region being a conventional reaction flow pipe. The reaction is carried out to a desired stage in the reaction vessel and then completed in the conventional reaction flow pipe. The reaction flow pipe is directly connected with the reaction vessel.

The formed benzotrifluoride can be conventionally separated from the reactants and catalyst, and then is purified by distillation.

Preferably, the reaction is conducted for a period of time between 55 and 75 minutes. There is little need to go beyond such a period of time as there is little increase in yield thereby.

The catalyst is preferably present in an amount between 10 and 100 ppm, based on the amount of benzotrichloride. Most preferably the catalyst is present in an amount between 40 and 70 ppm, based on the amount of benzotrichloride. The ratio of the aluminum chloride to the activated charcoal in the catalyst is preferably between 1:2.5 and 1:3.0. The ratio of the aluminum chloride to the activated charcoal in the catalyst is most preferably between 1:2.7 and 1:2.9. The catalyst is preferably prepared by suspending aluminum chloride and activated charcoal in an aqueous salt solution, drying the solution and activating the mixture of aluminum chloride and activated charcoal by heating at a temperature of about 300°C.

Benzotrifluoride is useful as an intermediate for making dyes and pharamceuticals, as a solvent and a dielectric fluid.

DETAILED DESCRIPTION OF THIS INVENTION

The catalyst according to this invention consists of a mixture of aluminum chloride and activated charcoal. Preferably there is a quantitative ratio of aluminum chloride to activated charcoal between 1:2.5 and 1:3.0 — although most preferably the ratio is between 1:2.7 and 1:2.9. The catalyst is preferably used in a quantity between 10 and 100 ppm (most preferably between 40 and 70 ppm), based upon the quantity of benzotrichloride used. The catalyst is preferably produced from aluminum chloride and activated charcoal (preferably of commercial quality) by suspending such in an aqueous hydrochloric acid, drying the solution, and activating the dried material at a temperature of around 300°C.

The reaction of the benzotrichloride with hydrogen fluoride is known; this invention involves unobvious innovations therein. The distillation processing (during reaction) of the reaction mixture is done according to known methods.

The reaction is preferably carried out in a pressure vessel which is equipped with a stirring mechanism.

Benzotrichloride is a liquid which boils at 213° to 214°C. and has a specific gravity of 1.38.

After insertion into the reactor of the benzotrichloride, phosphorous trichloride in a quantity of approximately 1 percent, related to the quantity of the benzotrichloride, is added thereto. This addition of phosphorous trichloride eliminates any possible small amount of water present and has an advantageous effect on the yield. (It is thought a reaction occurs with the starting material.)

After addition of the catalyst and hydrogen fluoride, the reaction components are heated to a temperature between 85° and 100°C. Preferably a temperature of 90° to 95°C. is used. In the case of temperatures above 100°C., the catalyst according to this invention quickly becomes inactivated; at temperatures below 85°C., the catalyst has not yet achieved its full activity. The pressure in the reactor is adjusted to 20 to 45 atm. Preferably a pressure of 35 to 40 atm. is used.

In order to be able to carry out the reaction successfully, an intensive intermixing or admixing of the reaction components is necessary. The measure of intermixing is characterized by the Reynolds number $Re$:

$$Re = \frac{n \cdot d^2}{v}$$

$n$ = revolutions per second of the stirrer
$d$ = diameter of the stirrer in meters
$v$ = kinematic viscosity in $m^2/sec$.

The numerical values for $Re$, according to the invention and resulting from it, amount to 65,000 and 100,000. Preferably the Reynolds number for the admixture is 80,000 to 90,000.

In the case of the process according to this invention it is sufficient to use hydrogen fluoride in stoichiometric quatities. Using such, yields of roughly 93 percent of benzotrifluoride result at a hydrogen fluoride conversion of roughly 96 to 97 percent. In the case of the use of a slight excess of hydrogen fluoride, which however should be a maximum excess of 10 percent related to the stoichiometrically necessary quantity, a yield of roughly 99 percent of benzotrifluoride is achieved (the conversion of hydrogen fluoride amounting to roughly 93 percent).

The small quantities of unreacted hydrogen fluoride are removed from the reaction together with the hydrogen chloride which forms during the reaction. A return for hydrogen fluoride is not necessary since such minimal quantities of unconverted hydrogen fluoride completely exit from the reaction vessel together with the hydrogen chloride which forms during the reaction.

The process according to this invention can also be carried out continuously. In such case, the reaction is carried out to a desired conversion percentage under the conditions according to this invention in a first reaction vessel and then the reaction mixture is placed into a second reaction vessel, with the reaction being carried under equal conditions to complete the conversion of the reaction components. A flow pipe can also be used instead of the second reaction vessel. Since, in the case of the reaction in the second stage, little hydrogen chloride is developed and little hydrogen fluoride is needed, the above mentioned disadvantages of the use of a flow pipe are of no consequence in the second stage.

The process according to this invention has the very substantial advantage of possessing a short reaction time. The optimum conversion and yield are achieved within 55 to 75 minutes. Most preferably a reaction time of about 70 minutes is used.

The benzotrifluoride formed can be removed in the customary manner from the reaction vessel after the reaction is completed. The benzotrifluoride can then be purified by distillation.

Herein all percentages, parts, ratios and proportions are on a weight basis, unless otherwise stated or otherwise obvious to one ordinarily skilled in the art.

EXAMPLE 1

391 gm of distilled benzotrichloride were inserted into a pressure-resistant 1-liter steel autoclave, having a sole-cooled reflux cooler, and heated to 95°C. Then 120 gm. of hydrogen fluoride were added while stirring and the pressure was raised with nitrogen to 40 atm. The hydrogen chloride developing during the reaction was continuously blown out by means of a pressure retention value into a washer after passing the cooler. After 70 minutes of reaction time the product was blown off by way of the bottom blow value, was washed with water and dried. Gas-chromotographic analysis of the organic product showed a content of 81 percent of benzotrifluoride and 18.7 percent of $\alpha$, $\alpha$-difluoro-$\alpha$-chlorotoluene.

EXAMPLE 2

This experiment was conducted according to the method of operation of Example 1, except that 50 ppm of the catalyst of this invention (having a quatitative ratio of aluminum chloride to activated charcoal of 1:2.7) was also added to the reaction zone. The blown off product was filtered, washed and dried. Gas-chromotographic analysis of the organic product showed a content of 92.8 percent of benzotrifluoride and 7 percent of $\alpha,\alpha$-difluoro-$\alpha$-chlorotoluene.

EXAMPLE 3

This experiment was conducted according to the method of operation of Example 1, except that 50 ppm of the catalyst according to this invention (having a quantitative ratio of aluminum chloride to activated charcoal of 1:2.7) was added and that 3 gm. of phosphorous trichloride was added to the benzotrifluoride before the other ingredients were added. Gas-chromotographic analysis of the organic product showed a content of 94 percent of benzotrifluoride and 5.7 percent of $\alpha,\alpha$-difluoro-$\alpha$-chlorotoluene.

EXAMPLE 4

This experiment was conducted according to the method of operation of Example 1, except that an excess of 7.5 percent related to the stoichiometrically necessary quantity). Also, 55 ppm of the catalyst of this invention (having a quantitative ratio of aluminum chloride to activated charcoal of 1:2.7) was added. Gas-chromotographic analysis of the organic product showed a content of 98.8 percent of benzotrifluoride and 1 percent of $\alpha,\alpha$-difluoro-$\alpha$-chlorotoluene.

What I claim is:

1. The process of preparing benzotrifluoride which comprises reacting benzotrichloride with hydrogen fluoride in a reaction zone at a pressure between 20 and 45 atm. and at a temperature between 85° and 100°C. in the presence of a catalyst consisting of a mixture of aluminum chloride and activated charcoal, the ratio of said aluminum chloride to said activated charcoal in said catalyst being between 1:2.5 and 1:3.0, on a stoichiometric basis, said hydrogen fluoride being 1.0 to 1.1 times the amount of said benzotrichloride, said benzotrichloride, said catalyst and said hydrogen fluoride being present as a mixture, and said mixture being intensively mixed to an extent during the reaction that the admixture or intermixture has a Reynolds number between 65,000 and 100,000.

2. The process of claim 1 wherein said benzotrichloride is placed in said reaction zone, and then said catalyst and said hydrogen fluoride are placed in said reaction zone.

3. The process of claim 2 wherein said benzotrichloride is treated with about one percent of phosphorous trichloride, based on said benzotrichloride, before said catalyst and said hydrogen fluoride are added to said reaction zone.

4. The process of claim 2 wherein said benzotrichloride is heated to said reaction temperature before said catalyst and said hydrogen fluoride are added to said reaction zone.

5. The process of claim 2 wherein said reaction zone is heated to said reaction temperature after said catalyst and said hydrogen fluoride are added to said reaction zone.

6. The process of claim 5 wherein the pressure in said reaction zone is raised to the reaction pressure after said reaction zone is heated to said reaction temperature.

7. The process of claim 5 wherein the pressure is raised in said reaction zone to said reaction pressure after addition of said benzotrichloride, said catalyst and said hydrogen fluoride by the introduction of an inert gas into said reaction zone.

8. The process of claim 7 wherein said inert gas is nitrogen.

9. The process of claim 1 wherein said reaction temperature is between 90° and 95°C.

10. The process of claim 1 wherein said reaction pressure is between 35 and 40 atmospheres.

11. The process of claim 1 wherein said benzotrichloride, said catalyst and said hydrogen fluoride are intensively mixed.

12. The process of claim 1 wherein said admixture has a Reynolds number between 80,000 and 90,000.

13. The process of claim 1 wherein said reaction is carried out continuously, said reaction zone comprises two separate reaction regions, and said reaction being carried out to a desired state in said first reaction region and being completed in said second reaction region.

14. The process of claim 1 wherein the reaction is conducted for a period of time between 55 and 75 minutes.

15. The process of claim 1 wherein the formed benzotrifluoride is conventionally separated from the reactants and catalyst and is purified by distillation.

16. The process of claim 1 wherein said catalyst is present in an amount between 10 and 100 ppm, based on the amount of said benzotrichloride.

17. The process of claim 1 wherein said catalyst is present in an amount between 40 and 70 ppm, based on the amount of said benzotrichloride.

18. The process of claim 1 wherein the ratio of said aluminum chloride to said activated charcoal in said catalyst is between 1:2.7 and 1:2.9.

19. The process of claim 1 wherein said catalyst is prepared by suspending aluminum chloride and activated charcoal in an aqueous hydrochloric acid, drying the solution and activating the mixture of aluminum chloride and activated charcoal by heating at a temperature of about 300°C.

* * * * *